(12) United States Patent
Eckman

(10) Patent No.: US 7,651,499 B2
(45) Date of Patent: Jan. 26, 2010

(54) WORKING CHANNEL FOR MINIMALLY INVASIVE SPINE SURGERY

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 0 days.

(21) Appl. No.: 11/258,800

(22) Filed: Oct. 26, 2005

(65) Prior Publication Data

US 2006/0089652 A1  Apr. 27, 2006

Related U.S. Application Data

(60) Provisional application No. 60/622,262, filed on Oct. 26, 2004.

(51) Int. Cl.
*A61F 5/00* (2006.01)
(52) U.S. Cl. .................................................. 606/86 R
(58) Field of Classification Search .............. 606/86, 606/86 R, 213, 90
See application file for complete search history.

(56) References Cited

U.S. PATENT DOCUMENTS

| | | | | |
|---|---|---|---|---|
| 3,624,800 | A | * | 11/1971 | Swick ........................ 251/4 |
| 4,959,058 | A | | 9/1990 | Michelson |
| 4,973,321 | A | | 11/1990 | Michelson |
| 5,015,247 | A | | 5/1991 | Michelson |
| 5,171,279 | A | * | 12/1992 | Mathews .................... 128/898 |
| 5,423,825 | A | * | 6/1995 | Levine ....................... 606/86 |
| 5,437,683 | A | * | 8/1995 | Neumann et al. .......... 606/151 |
| 5,484,437 | A | | 1/1996 | Michelson |
| D374,287 | S | * | 10/1996 | Goble et al. ............... D24/145 |
| 5,643,320 | A | | 7/1997 | Lower et al. |
| 5,772,661 | A | | 6/1998 | Michelson |
| 5,976,146 | A | * | 11/1999 | Ogawa et al. ............. 606/86 R |
| 6,048,339 | A | | 4/2000 | Zirps et al. |
| 6,053,907 | A | | 4/2000 | Zirps |
| 6,080,155 | A | | 6/2000 | Michelson |
| 6,083,228 | A | | 7/2000 | Michelson |
| 6,159,179 | A | | 12/2000 | Simonson |
| 6,159,214 | A | | 12/2000 | Michelson |
| 6,187,000 | B1 | | 2/2001 | Davison et al. |
| 6,241,734 | B1 | * | 6/2001 | Scribner et al. ............ 606/93 |
| 6,283,973 | B1 | | 9/2001 | Hubbard et al. |

(Continued)

FOREIGN PATENT DOCUMENTS

WO  2004021899 A1  3/2004

(Continued)

*Primary Examiner*—Pedro Philogene
(74) *Attorney, Agent, or Firm*—Panitch Schwarze Belisario & Nadel LLP

(57) ABSTRACT

A working channel for spinal surgery includes a body having a distal end, a proximal end and an interior lumen traversing through the elongate body. The elongate body generally has a parallelogram-shaped cross-section. Another working channel for spinal surgery includes a flared upper section having a distal end, a proximal end and an interior lumen traversing through the flared upper section. The proximal end of the flared upper section is wider than the distal end of the flared upper section. The working channel also includes a lower section extending from the distal end of the flared upper section. The lower section has a distal end, a proximal end and an interior lumen traversing through the lower section. The lower section generally has a parallelogram-shaped cross-section.

26 Claims, 6 Drawing Sheets

U.S. PATENT DOCUMENTS

| | | |
|---|---|---|
| 6,361,488 B1 | 3/2002 | Davison et al. |
| 6,508,821 B1 | 1/2003 | Schwartz et al. |
| 6,524,320 B2 | 2/2003 | DiPoto |
| 6,530,880 B2 | 3/2003 | Pagliuca |
| 6,530,926 B1 | 3/2003 | Davison |
| 6,547,795 B2 | 4/2003 | Schneiderman |
| 6,554,836 B2 * | 4/2003 | Michelson .................. 606/86 |
| 6,652,553 B2 | 11/2003 | Davison et al. |
| 6,692,501 B2 | 2/2004 | Michelson |
| 6,800,084 B2 | 10/2004 | Davison et al. |
| 6,821,243 B2 | 11/2004 | Pagliuca et al. |
| 6,896,680 B2 | 5/2005 | Michelson |
| 6,916,330 B2 | 7/2005 | Simonson |
| 6,929,606 B2 | 8/2005 | Ritland |
| 6,951,538 B2 | 10/2005 | Ritland |
| 6,986,772 B2 | 1/2006 | Michelson |
| 7,008,431 B2 | 3/2006 | Simonson |
| 7,033,362 B2 * | 4/2006 | McGahan et al. ............. 606/96 |
| 7,056,321 B2 | 6/2006 | Pagliuca et al. |
| 7,074,226 B2 * | 7/2006 | Roehm et al. ................ 606/90 |
| 7,217,246 B1 * | 5/2007 | Stone ........................ 600/585 |
| 2002/0177897 A1 | 11/2002 | Michelson |
| 2003/0032962 A1 * | 2/2003 | McGahan et al. ............. 606/80 |
| 2003/0083642 A1 * | 5/2003 | Boyd et al. ................ 604/506 |
| 2003/0083688 A1 | 5/2003 | Simonson |
| 2003/0153927 A1 | 8/2003 | DiPoto et al. |
| 2003/0199874 A1 | 10/2003 | Michelson |
| 2004/0073213 A1 | 4/2004 | Serhan et al. |
| 2004/0116954 A1 | 6/2004 | Pagliuca et al. |
| 2004/0230100 A1 | 11/2004 | Shluzas |
| 2004/0230309 A1 | 11/2004 | DiMauro et al. |
| 2005/0070900 A1 | 3/2005 | Serhan et al. |
| 2005/0071012 A1 | 3/2005 | Serhan et al. |
| 2005/0075540 A1 | 4/2005 | Shluzas et al. |
| 2005/0075644 A1 | 4/2005 | DiPoto et al. |
| 2005/0080418 A1 | 4/2005 | Simonson et al. |
| 2005/0090822 A1 | 4/2005 | DiPoto |
| 2005/0090833 A1 | 4/2005 | DiPoto |
| 2005/0090899 A1 | 4/2005 | DiPoto |
| 2005/0107789 A1 | 5/2005 | Sweeney |
| 2005/0131421 A1 | 6/2005 | Anderson et al. |
| 2005/0137461 A1 | 6/2005 | Marchek et al. |
| 2005/0154389 A1 | 7/2005 | Selover et al. |
| 2005/0159650 A1 | 7/2005 | Raymond et al. |
| 2005/0159651 A1 | 7/2005 | Raymond et al. |
| 2005/0171551 A1 | 8/2005 | Sukovich et al. |
| 2005/0192589 A1 | 9/2005 | Raymond et al. |
| 2005/0215866 A1 | 9/2005 | Kim |
| 2005/0245942 A1 | 11/2005 | DiPoto |
| 2005/0251192 A1 * | 11/2005 | Shluzas et al. .............. 606/191 |
| 2005/0251196 A1 | 11/2005 | Wong |
| 2005/0273131 A1 | 12/2005 | Shluzas et al. |
| 2005/0273132 A1 | 12/2005 | Shluzas et al. |
| 2005/0273133 A1 | 12/2005 | Shluzas et al. |
| 2006/0030858 A1 | 2/2006 | Simonson et al. |
| 2006/0030861 A1 | 2/2006 | Simonson et al. |
| 2006/0069404 A1 | 3/2006 | Shluzas et al. |
| 2006/0084981 A1 | 4/2006 | Shluzas |
| 2006/0095039 A1 | 5/2006 | Mutchler |

FOREIGN PATENT DOCUMENTS

| | | |
|---|---|---|
| WO | 2005084572 A2 | 9/2005 |
| WO | 2006052819 A2 | 5/2006 |
| WO | 2006058079 A2 | 6/2006 |

* cited by examiner

| Round Tubes | | | | |
|---|---|---|---|---|
| | 14 mm | 16 mm | 18 mm | 22 mm |
| Circumference ($2\pi r$) | 43.98 mm | 50.27 | 56.55 | 69.12 |
| Surface Area ($\pi r^2$) | 153.94 mm² | 201.06 | 254.47 | 380.13 |
| Parallelogram Working Channels | | |
|---|---|---|
| $L_x \times W_x$ | 22 x 18 | 24 x 20 |
| Perimeter Equivalent to Circumference (2 sides + 2 sides) | 58 mm | 62 mm |
| Surface Area Base x Altitude(height) | 210 mm² | 240 mm² |
*FIG. 9*
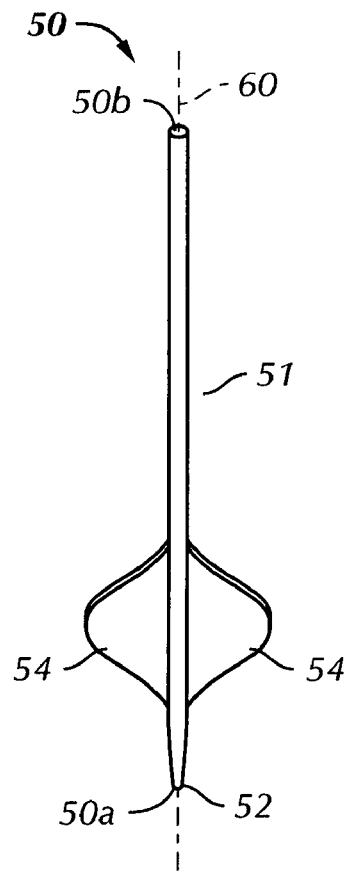
*FIG. 10*
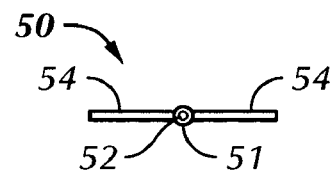
*FIG. 11*

WORKING CHANNEL FOR MINIMALLY INVASIVE SPINE SURGERY

CROSS REFERENCE TO RELATED APPLICATIONS

This application claims priority to U.S. Provisional Patent Application No. 60/622,262 filed on Oct. 26, 2004, entitled "Working Channel for Minimally Invasive Spine Surgery."

BACKGROUND OF THE INVENTION

The present invention relates to an apparatus and method for performing spine surgery, and more particularly, to a working channel for minimally invasive spine surgery and a method for using the working channel.

Referring to prior art FIGS. 1A and 1B, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branch off to various areas of the body for the purposes of motor control, sensation, or the like. The spine 120 includes seven cervical vertebrae (not shown), twelve thoracic vertebrae (not shown), five lumbar vertebrae, $L^I$-$L^V$, five sacral vertebrae, $S^I$-$S^V$, and three coccyx vertebrae 126. The sacral and coccyx vertebrae are each fused, thereby functioning as a single unit. FIG. 1B shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 1A, directional arrow 101a is pointing in the posterior direction and directional arrow 101b is pointing in the anterior direction. FIG. 1A shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar to the smallest coccyx vertebrae 126. Each vertebrae 100 further includes two transverse processes 104 located on either side and a protective plate-like structure referred to as a lamina 110. Nerves from the spinal cord 128 pass through the spinal canal 108 and foramina 111 to reach their respective destinations within the body.

Recently, less invasive surgical techniques referred to as "minimally invasive" surgery have been developed to reduce the surgical trauma to a patient during spine surgery. In minimally invasive surgery, a much smaller incision is made than in normal open surgeries. A small retractor, working channel or tube is inserted through the posterior muscles (not shown) to allow access to the spine. Surgeons utilize special surgical instruments modified to work in such small openings such as curettes, osteotomes, reamers, probes, retractors, forceps or the like to access the spine while monitoring their technique using a microscope, fluoroscope (real-time X-ray monitoring), and/or an endoscope (a miniature TV camera with associated viewing monitor).

In order to access the area of interest in a minimally invasive spinal surgery, a working tube is installed through an incision in a patient's back. Presently available working tubes are typically round or ovoid. The round or ovoid shape places pressure on the skin in the area around an incision because the incisions are typically linear. Additionally, the round shape restricts access with surgical instruments between spinous processes and between pedicle and facet structures, thereby restricting possible movement of the instruments. Even further, the round shape makes moving the working tube along the sagittal plane difficult because of the large amount of surface area that is being pressed against muscle.

It is desirable to provide a working channel for minimally invasive spine surgery and a method for using such a working channel in order to allow access by a surgical instrument for performing minimally invasive spinal surgeries. The working channel should be easy to use, safe to insert into the body during surgery, provide for improved access and should not cause undesired damage to adjacent vertebrae. It is desirable to provide a minimally invasive surgical technique that allows for fast patient recovery times and that can be used on an outpatient basis.

BRIEF SUMMARY OF THE INVENTION

Briefly stated, the present invention comprises a working channel for minimally invasive spine surgery and a method for using the working channel.

The present invention further comprises a working channel for spinal surgery that includes an elongate body having a distal end, a proximal end and an interior lumen traversing through the elongate body. The elongate body generally has a parallelogram-shaped cross-section.

The present invention further comprises a working channel for spinal surgery that includes a flared upper section having a distal end, a proximal end and an interior lumen traversing through the flared upper section. The proximal end of the flared upper section is wider than the distal end of the flared upper section. The working channel also includes a lower section extending from the distal end of the flared upper section. The lower section has a distal end, a proximal end and an interior lumen traversing through the lower section. The lower section generally has a parallelogram-shaped cross-section.

The present invention also comprises a working tube/channel for spinal surgery including a body having a distal end, a proximal end and an interior lumen traversing through the elongate body. The body includes a slot at the distal end.

The present invention also comprises a method of using a working channel in outpatient spine surgery that includes making an incision between about 10 mm and about 100 mm in span proximate a first vertebra and a second vertebra of a spine of the patient. The incision is off-center with respect to the posterior-side of the spine of the patient and proximate to one of the laminae and the foramen of the first and second vertebrae. A distal end of the working channel is inserted into the incision to a desired depth proximate the first vertebra and the second vertebra of the spine accessible through the incision. The working channel generally has a parallelogram-shaped cross-section. One of the first vertebra, the second vertebra and a small gap between the first and second vertebrae are accessed through the working channel.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 9 is a table comparing the circumference and surface area of a conventional round working tube to the perimeter measurement and surface area of a working channel in accordance with the preferred embodiments of the present invention;

FIG. 10 is a side elevational view of a fascia knife for use in accessing the spine in minimally invasive procedures in accordance with the preferred embodiments of the present invention; and FIG. 11 is a top plan view of the fascia knife of FIG. 10.

DETAILED DESCRIPTION OF THE INVENTION

Figure 1A:
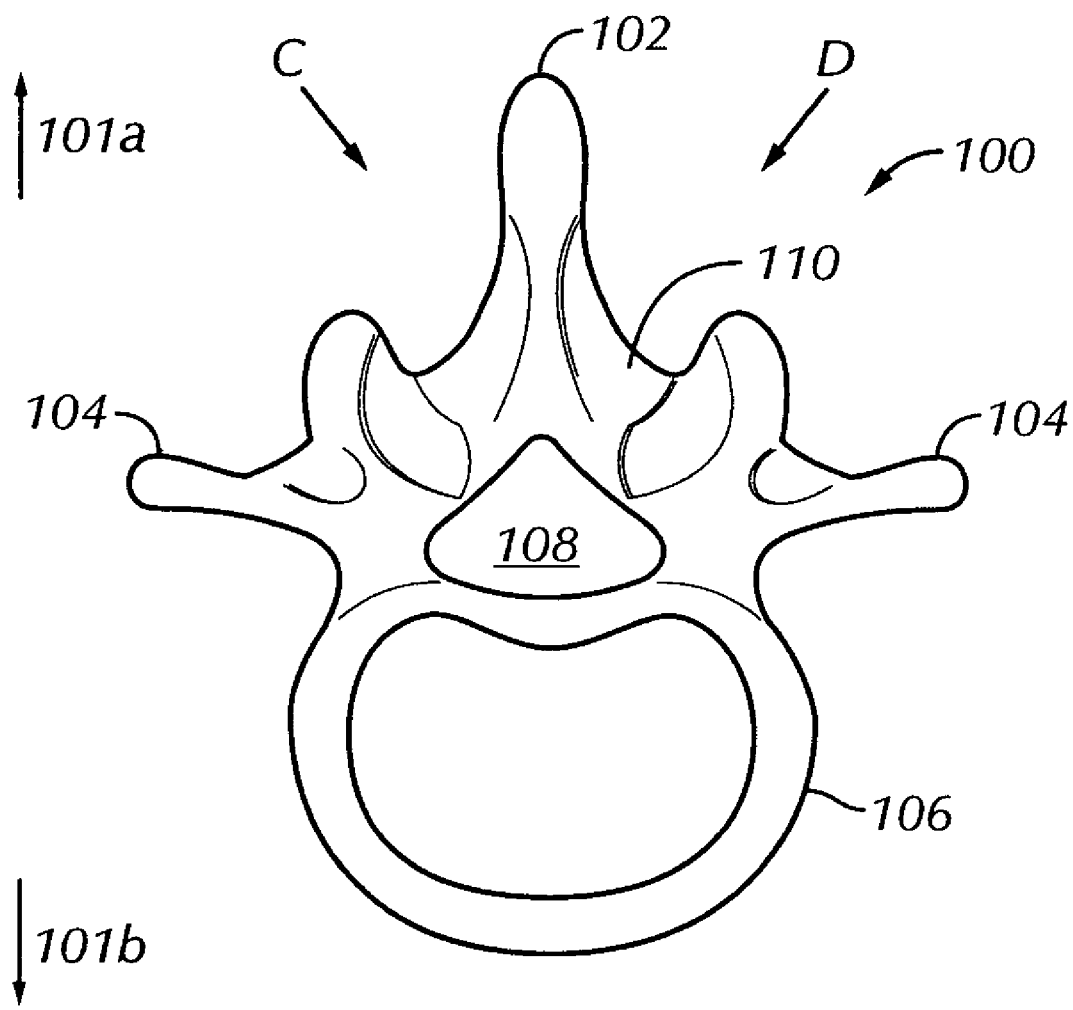
FIG. 1A is a top sectional view of a human vertebrae as is known in the art.
Figure 1B:
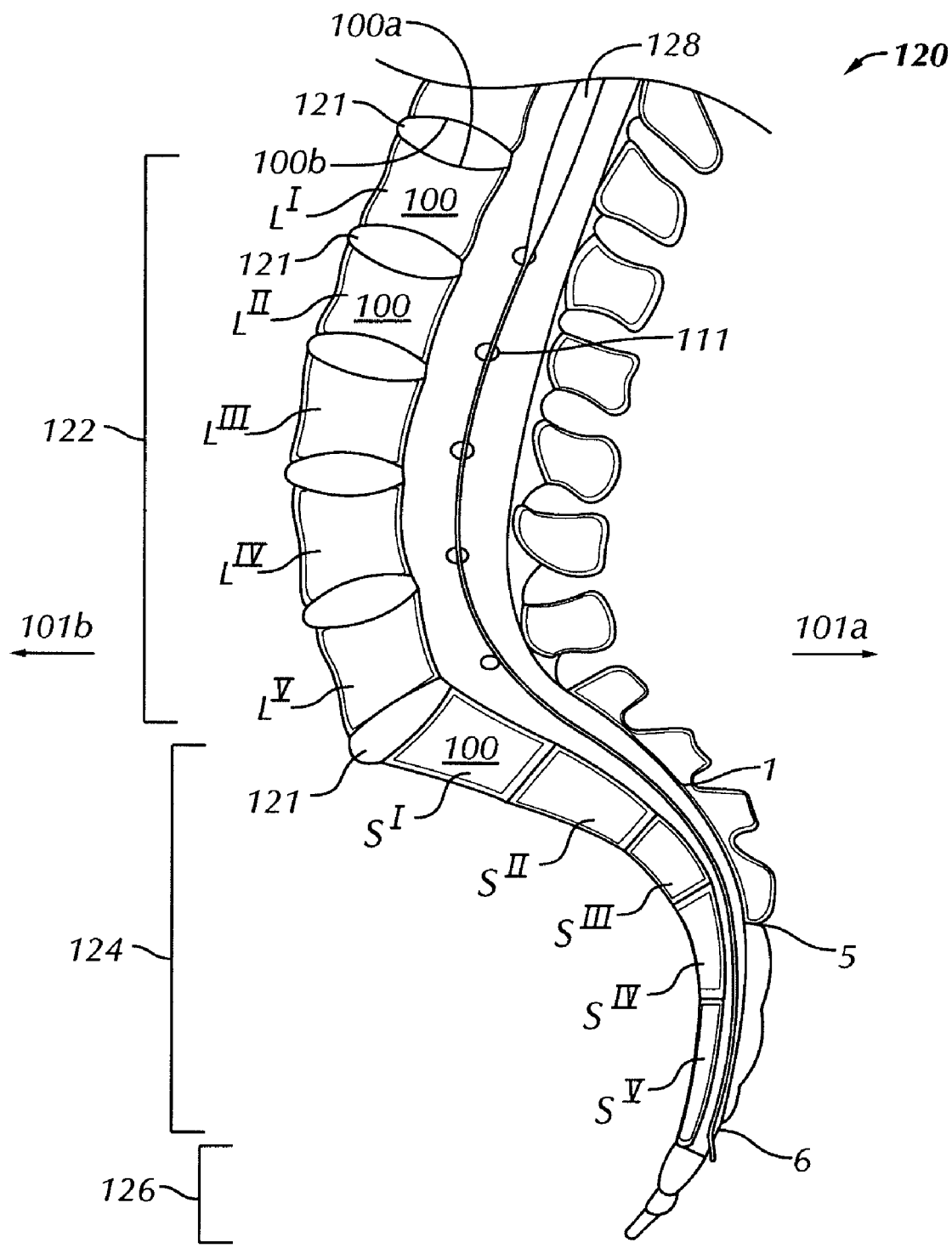
FIG. 1B is a side sectional view of the lumbar and sacral regions of a human spine as in known in the art.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the object described and designated parts thereof. The terminology includes the words above specifically mentioned, derivatives thereof and words of similar import. Additionally, the word "a", as used in the claims and in the corresponding portions of the specification, means "at least one."

Referring to the drawings in detail, wherein like reference numerals indicate like elements throughout, FIGS. 2-5 show a working channel 18 for spinal surgery in accordance with a first preferred embodiment of the present invention. The working channel 18 includes an elongate body 20 having a distal end 20a, a proximal end 20b and an interior lumen 20c traversing through the elongate body 20.

Figure 3:
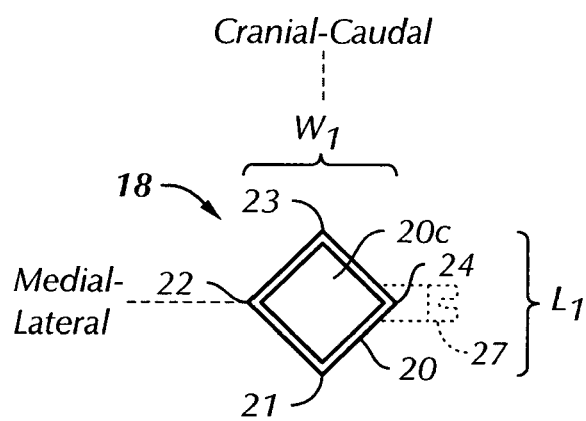
FIG. 3 is a top sectional view of a portion of the working channel of FIG. 2.

The elongate body 20 has a generally parallelogram-shaped cross-section (see FIG. 3). The parallelogram-shaped cross-section includes a first corner 21, a second corner 22, a third corner 23 and a fourth corner 24. The first and third corners 21, 23 are generally intended to point in the cranial and caudal directions of a patient, while the second and forth corners 22, 24 are generally intended to face the lateral and medial directions of a patient with respect to the posterior side of the patient. As shown in FIG. 3, the parallelogram-shaped cross-section includes four corners 21-24 that are generally pointed. Preferably, the cross-section of the interior lumen 20c defined by the elongate body 20 is similar to the cross-section of the outer periphery of the elongate body 20. Preferably, inner and outer cross-sections of the elongate body 20 taken along imaginary planes extending through the elongate body 20 and generally perpendicular to the walls of the elongate body 20 are dimensionally matched, meaning the relationship between the inner and outer cross-sections is the same at each point along a length of a longitudinal axis (not shown) extending from the distal end 20a to the proximal end 20b of the elongate body 20. Preferably, walls of the elongate body 20 should be as thin as possible in order to maximize the access or working space available within the working channel 18.

The parallelogram-shaped outer cross-section of the elongate body 20 has a width $W_1$ as measured between the second and fourth corners 22, 24 and a sagittal length $L_1$ as measured between the first and third corners 21, 23. The width $W_1$ and sagittal length $L_1$ may be the same or different. The width $W_1$ may be greater than the sagittal length $L_1$ or the width $W_1$ may be less than the sagittal length $L_1$. Preferably, the width $W_1$ is slightly less than the sagittal length $L_1$. For example, the width $W_1$ may be about 18 mm and the sagittal length $L_1$ may be about 22 mm, or the width $W_1$ may be about 20 mm and the sagittal length $L_1$ may be about 24 mm.

The working channel 18 is preferably configured to be inserted through an incision less than about 50 mm in span. The working channel 18 may even be configured to be inserted through an incision less than about 25 mm in span or greater than about 50 mm in span. The elongate body 18 preferably is between about 5 mm and 30 mm in dimension as measured across cranial-caudal dimensions (sagittal length $L_1$) and the medial-lateral dimensions (width $W_1$), making it ideally suited for use in outpatient minimally invasive surgery.

In an alternate of the first preferred embodiment, a width $W_1$ and/or sagittal length $L_1$ of the proximal end 20b is greater than a width $W_1$ and/or sagittal length $L_1$ of the distal end 20a of the elongate body 20 (not clearly shown). The slope of the sidewalls may vary along the depth between the proximal end 20b and the distal end 20a in a linear or non-linear fashion creating other unique insertion mechanisms while improving exterior accessibility.

Figure 2:
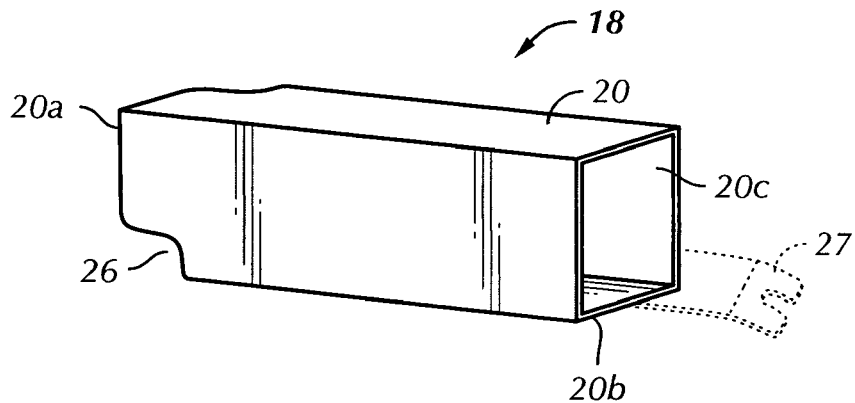
FIG. 2 is a perspective view of a working channel in accordance with a first preferred embodiment of the present invention.
Figure 4:
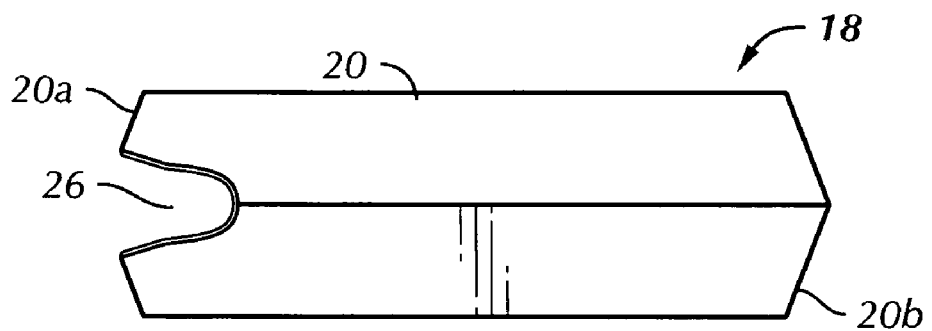
FIG. 4 is a cranial or caudal side elevational view of the working channel of FIG. 2.
Figure 5:
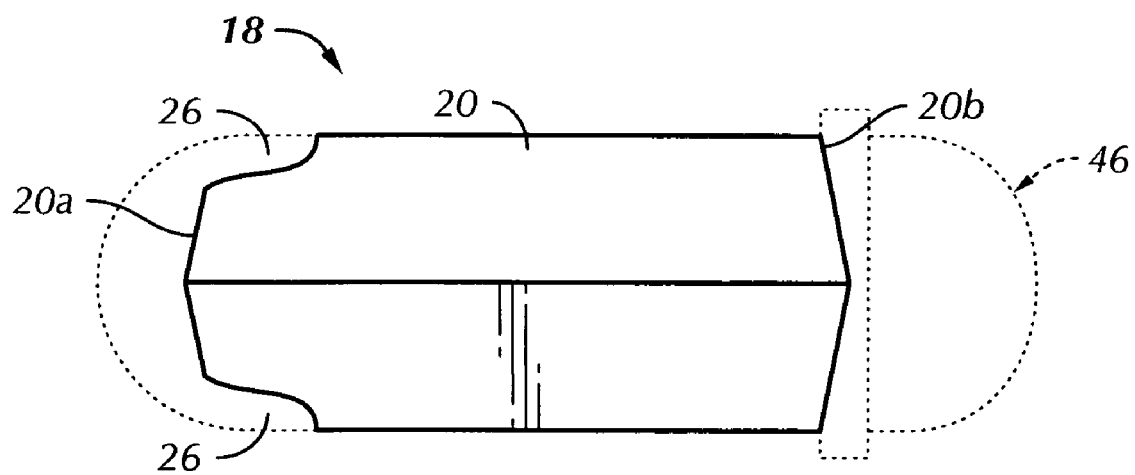
FIG. 5 is a medial or lateral side elevational view of the working channel of FIG. 2.

FIG. 4 is a cranial or caudal side elevational view of the working channel 18, and FIG. 5 is a medial or lateral side elevational view of the working channel of FIG. 2. As shown in FIGS. 2 and 4-5, the working channel 18 optionally includes slots 26 in the cranial-caudal sides.

Figure 6:
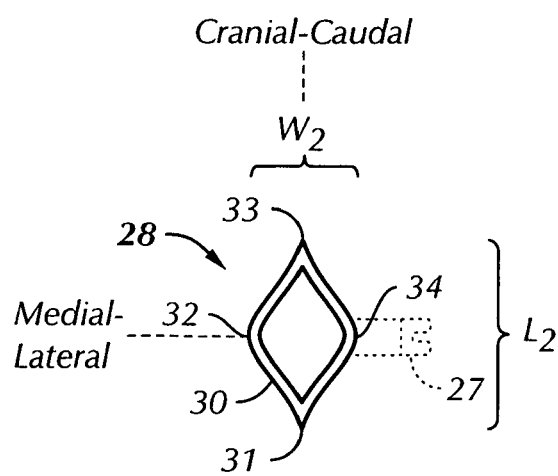
FIG. 6 is a top sectional view of a portion of a working channel in accordance with a second preferred embodiment of the present invention.

FIG. 6 is a top cross sectional view of a working channel 28 in accordance with a second preferred embodiment of the present invention. The outer cross-section of the working channel 28 of FIG. 6 is similar to the outer cross-section of the working channel 18 of FIG. 3 except that the medial and lateral sides are generally rounded. The working channel 28 has an elongate body 30 that has a generally parallelogram-shaped outer cross-section. The parallelogram-shaped outer cross-section has first, second, third and fourth corners 31, 32, 33, 34. The first and third corners 31, 33 are generally pointed and the second and forth corners 32, 34 are generally rounded. Thus, the second and forth corners 32, 34 each have a radius of curvature. Alternatively, the parallelogram-shaped outer cross-section may include four corners 31-34 that are generally rounded, and therefore, the four corners 31-34 would each have a radius of curvature. Preferably, the cross-section of the interior lumen 30c defined by the elongate body 30 is similar to the cross-section of the outer periphery of the elongate body 30. Preferably, walls of the elongate body 30 should be as thin as possible in order to maximize the access or working space available within the working channel 28.

The working channel 28 is preferably configured to be inserted through an incision less than about 50 mm in span. The working channel 28 may even be configured to be inserted through an incision less than about 25 mm in span or greater than about 50 mm in span. The elongate body 28 preferably is between about 5 mm and 30 mm in width $W_2$ and sagittal length $L_2$, making it ideally suited for use in outpatient minimally invasive surgery.

The parallelogram-shaped outer cross-section of the elongate body 30 has a width $W_2$ as measured between the second and fourth corners 32, 34 and a sagittal length $L_2$ as measured between the first and third corners 31, 33. The width $W_2$ and sagittal length $L_2$ may be the same or different. The width $W_2$ may be greater than the sagittal length $L_2$ or the width $W_2$ may be less than the sagittal length $L_2$. Preferably, the width $W_2$ is slightly less than the sagittal length $L_2$. For example, the width $W_2$ may be about 18 mm and the sagittal length $L_2$ may be about 22 mm, or the width $W_2$ may be about 20 mm and the sagittal length $L_2$ may be about 24 mm.

In an alternate of the second preferred embodiment, a width $W_2$ and/or sagittal length $L_2$ of the proximal end 20b is greater than a width $W_2$ and/or sagittal length $L_2$ of the distal end 20a of the elongate body 20 (not clearly shown). The slope of the sidewalls may vary along the depth in a linear or non-linear fashion creating other unique insertion mechanisms while improving exterior accessibility.

Figure 7:
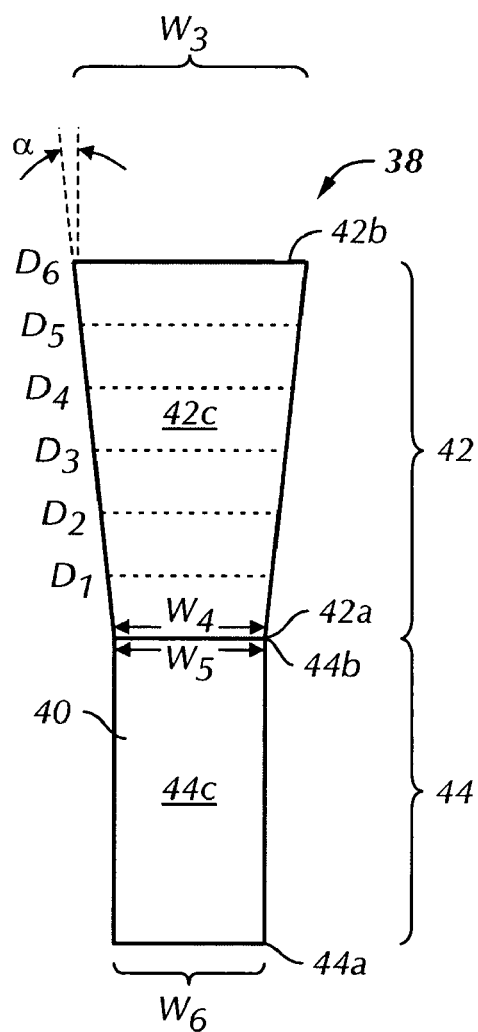
FIG. 7 is a side sectional view of a working channel in accordance with a third preferred embodiment of the present invention.

FIG. 7 is a side sectional view of a working channel 38 for spinal surgery in accordance with a third preferred embodiment of the present invention. The working channel 38 includes a flared upper section 42 having a distal end 42a, a proximal end 42b and an interior lumen 42c traversing through the flared upper section 42. The flared upper section 42 generally has a parallelogram-shaped outer cross-section similar to the first and/or second preferred embodiments. The flared upper section 42 may have other outer cross-section shapes such as ovoid, square, round, rectangular, polygonal or the like. The proximal end 42b of the flared upper section 42 has a width $W_3$ that is wider than a width $W_4$ of the distal end 42a of the flared upper section 42. The flared upper section 42 slopes inwardly from the proximal end 42b toward the distal end 42a at an angle $\alpha$ with respect to a vertical axis. Preferably, the angle $\alpha$ is between about 3°-20° with respect to a vertical axis.

The flared upper section 42 may come in a variety of overall depths $D_1$-$D_6$ depending on the application. The depths $D_1$-$D_6$ may vary from may 1 to 6 centimeters (cm). The lower section 44 will be about 3-6 cm, but preferably the lower section 44 will be about 5 cm in depth. Thus, the overall working channel 38 can vary from 4-12 cm in depth.

The working channel 38 also includes a lower section 44 extending from the distal end 42a of the flared upper section 42. The lower section 44 has a distal end 44a, a proximal end 44b and an interior lumen 44c traversing through the lower section 44. The lower section is going to be about 5 cm in depth. The lower section 44 generally has a parallelogram-shaped outer cross-section as well, similar to the first and second preferred embodiments. A width $W_5$ of the proximal end 44b of the lower section 44 is generally about the same as the width $W_4$ of the distal end 42a of the flared upper section 42. The lower section 44 preferably has a generally uniform width $W_5$,$W_6$ along the depth between the distal end 44a and the proximal end 44b of the lower section 44. However, the lower section 44 may also be slightly flared so that the width $W_5$ at the proximal end 44b is slightly greater or less than a width $W_6$ at the distal end 44a. Further, the slope of the flare as well as the cross-sectional shape of the lower section 44 may be different than that of the flared upper section 42, being similar in some ways to a two-stage funnel. Preferably, the cross-section of the interior lumen 44c defined by the lower section 44 is similar to the cross-section of the outer periphery of the lower section 44. Preferably, walls of the elongate body 40 should be as thin as possible in order to maximize the access or working space available within the working channel 38.

The flared upper section 42 and the lower section 44 are preferably formed as a one-piece elongate body 40. The one-piece elongate body 40 may be formed of molded or machined metal, alloys, polymeric material or the like.

The flared upper section 42 eases accessibility with long instruments, drills, endoscopes, suction tools, electrosurgical instruments or multiple instruments used in spine surgery. The reason for the flaring is that as the length of the elongate body 40 increases, the approach angle, angles of motion of instruments, the ability to perform dexterous tasks and visibility all diminish. Preferably, the flaring begins at an elevation that is beyond the muscle layer such as at the subcutaneous fat layer and skin or beyond. The flared upper section makes it much more feasible to conduct minimally invasive surgery for overweight patients.

The working channels 18, 28, 38 are preferably configured to be inserted through an incision between about 5 mm and about 100 mm in span, but is more preferably configured to be inserted through an incision of about 25-50 mm in span. Of course, the working channels 18, 28, 38 can be configured to be inserted through incisions or openings having other dimensions and can be used in conventional open surgery without departing from the present invention.

The portions of the working channels 18, 28, 38 intended to contact internal human body matter are formed of a biologically compatible material such as stainless steel, titanium, nickel plated metal, any biocompatible metal or alloy, a biocompatible ceramic, a biocompatible polymeric material or the like. Preferably, the working channels 18, 28, 38 are unitary structures that are molded or cast. The working channels 18, 28, 38 may also be formed of a clear polymeric material allowing for insulation from electrosurgical procedures such as cutting and/or coagulating and for increasing the field of view.

The working channels 18, 28, 38 also optionally include a slot 26 at the distal-most portion of the working channels 18, 28, 38 in the cranial-caudal sides for allowing more complex dexterous work to be performed in the confined area required by minimally invasive surgery such as screwing in pedicle screws, attaching fixation devices, tightening hardware or the like. This slot 26 could be applied to any shape working channel 18, 28, 38 or conventional working tube to improve the ability to move within the sagittal plane over pedicle screws and other attachment mechanisms extending out of vertebral bone.

The working channels 18, 28, 38 need not be a strict parallelogram-shaped cross-section, but rather, the "corners" 21-24, 31-34 where the side walls meet may be slightly or rounded or even chamfered.

Figure 8:
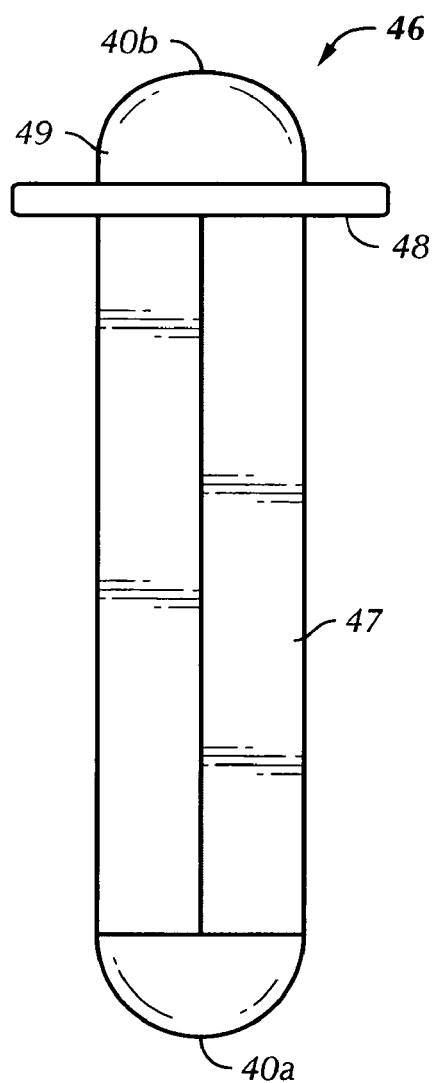
FIG. 8 is a side elevational view of an insertion tool for use with the preferred embodiments of the present invention.

FIG. 8 shows an insertion tool 46 for use with the preferred embodiments of the present invention. The insertion tool 46 has a distal end 46a and a proximal end 46b. The insertion tool 46 includes an elongate body 47 and a handle 49. Optionally, the insertion tool 46 can include a flange 48 to assist in pushing the working channel 18, 28, 38. The elongate body 47 is preferably shaped similar in cross-section to the respective working channel 18, 28, 38. The distal end of the working channel 18, 28, 38 may have a chamfered, radiused or ramped edge to blend with the elongate body 47 of the insertion tool 46. FIG. 5 shows the insertion tool 46 in phantom disposed inside the lumen 18c of the working channel 18 until the flange 48 engages the proximal end 20b of the working channel 18. The insertion tool 46 makes it easier to install the working channel 18, 28, 38 into an incision without the need to use time-consuming dilators (not shown) or the like. The insertion tool 46 may be formed of molded or machined metal, alloys, polymeric material or the like. However, the working channels 18, 28, 38 of the present invention can also be used with dilators.

FIGS. 10-11 show a fascia knife 50 for use in accessing the spine 120 in minimally invasive procedures in accordance with the preferred embodiments of the present invention. The fascia knife 50 has a distal end 50a and a proximal end 50b. The fascia knife 50 includes an elongate body 51 and an interior capillary 52. The interior capillary lumen 52 is configured to slidingly receive a surgical pin 60 (shown in phantom in FIG. 10), such as a Steinman pin. The interior capillary lumen 52 should preferably, but need not, extend entirely through the elongate body 51. The elongate body 51 has a diameter of about 2-5 mm and the blades 54 have a maximum span of about 5-25 mm. Preferably, the blades 54 are set-back about 2-2.5 cm from the distal end 50a of the fascia knife 50. Preferably, the blades 54 are sharpened in the distal direction and they reach their maximum span in 2-2.5 cm. Since the muscle is approximately 4-5 cm in depth, the blades 54 will need to begin cutting at an insertion depth of about 2-2.5 cm and need to complete cutting at an insertion depth of about 4-5 cm as measured from the distal end 52a of the fascia knife 50.

The working channel 18, 28, 38 is preferably used in outpatient spinal surgery. For example, in one method of using the working channel 18, 28, 38 in outpatient surgery, a surgeon makes an incision between about 10 mm and about 100 mm in span proximate a first vertebra 100 and a second vertebra 100 of a spine 129 of the patient. The incision is off-center with respect to the posterior-side of the spine 120 of the patient and is proximate to one of the laminae and the foramen 104 of the first and second vertebrae 100. A distal end 20a, 44a of the working channel 18, 28, 38 is inserted into the incision to a desired depth proximate the first vertebra and the second vertebra 100 of the spine 120 accessible through the incision. The working channel 18, 28, 38 generally has a parallelogram-shaped outer cross-section. One of the first vertebra 100, the second vertebra 100 and a small gap between the first and second vertebrae 100 are accessed through the working channel 18, 28, 38. Optionally, before inserting the working channel 18, 28, 38, the surgeon may use a finger or a blunt surgical instrument (not shown) smaller than the working channel 18, 28, 38 to gently move apart fat, muscle, tendons or the like.

In another method of using a working channel 18, 28, 38 in outpatient spine surgery, a surgeon inserts a distal end of a surgical pin 60 in a posterior region of a patient proximate the small gap between the first vertebra 100 and the second vertebra 100 of the spine 120 accessible through the incision. The surgeon then makes an incision between about 10 mm and about 100 mm in span in a posterior region of a patient proximate a small gap between a first vertebra 100 and a second vertebra 100 of a spine 120 of the patient. The small gap is preferably off-center with respect to the posterior-side of the spine 120 of the patient and proximate to the laminae or a foramen 104 of the first and second vertebrae 100. The surgeon slips the fascia knife 50 over the surgical pin 60 such that the interior capillary lumen 52 of the fascia knife 50 receives the surgical pin 60. As the surgeon moves the fascia knife 50 distally, the blades 54 of the fascia knife 50 cut through fascia covering the paraspinal muscles providing easier access for the working channel 18, 28, 38. The surgeon then removes the fascia knife 50 and surgical pin 60. The surgeon inserts the combination of the working channel 18, 28, 38 and the insertion tool 46 to the desired depth and then removes the insertion tool 46 leaving the working channel 18, 28, 38 for accessing the spine 120. The surgeon can then slide the working channel 18, 28, 38 along the cranial and caudal directions.

In yet another method of using a working channel 18, 28, 38 in outpatient spine surgery, the surgeon can insert a distal end of a dilator (not shown) over the surgical pin 60 proximate the small gap between the first vertebra 100 and the second vertebra 100 of the spine 120 accessible through the incision. The surgeon may remove the surgical pin 60 at this time or later. More than likely, the surgeon will need to successively insert a plurality of increasingly larger dilators over the previous dilator proximate the small gap between the first vertebra 100 and the second vertebra 100 of the spine 120 accessible through the incision, in order to gently expand the area of interest. Preferably, each dilator generally has a parallelogram-shaped outer cross-section similar to the working channel 18, 28, 38. But, the dilator may be other shapes without departing from the invention. The surgeon inserts a distal end 20a, 44a of the working channel 18, 28, 38 over the dilator proximate the small gap between the first vertebra 100 and the second vertebra 100 of the spine 120 accessible through the incision. The working channel 18, 28, 38 generally has a parallelogram-shaped outer cross-section, as mentioned above, thereby being eased over the dilator(s) which had previously expanded (dilated) the fascia and muscle in the area of interest. The surgeon removes the dilator(s) and the surgical pin 60 through the working channel 18, 28, 38. The working channel 18, 28, 38 permits the surgeon to access one of the first vertebra 100, the second vertebra 100 and a small gap between the first vertebra 100 and the second vertebra 100 of the spine 120 for performing a surgical procedure or investigation.

Because a parallelogram-shaped outer cross-section working channel 18, 28, 38 has a smaller perimeter, there is less pressure on skin edges as compared to conventional round or ovoid working tubes. Because a parallelogram-shaped outer cross-section working channel 18, 28, 38 has a smaller surface area, it allows less muscle displacement as compared to conventional round or ovoid working tubes, and therefore, results in less bleeding and pain once the working channel 18, 28, 38 is removed. FIG. 9 is a comparison of the perimeter (circumference) and surface area of a conventional round working tube to the perimeter measurement and surface area of a working channel 18 in accordance with the preferred embodiments of the present invention. Obviously, the working channel 28 has a non-geometric shape whose surface area would require much more complicated area calculations using software; however the parallelogram-shape can roughly approximate its surface area.

Additionally, the parallelogram-shaped outer cross-section of the working channel 18, 38 provides less resistance when performing sliding movements along or parallel to the sagittal plane or axis. The working channel 28 of the second preferred embodiment has a parallelogram-shaped outer cross-section (FIG. 4) with at least two rounded corners 32, 34, and the rounded corners 32, 34 (inserted at the medial and lateral sides) provide even less resistance when moving cranially-caudally within the incision (i.e., like a boat keel cutting through water). The muscle and tissue are gently pushed apart by the parallelogram-shaped outer cross-section instead of being bluntly shoved by a conventional round tube which typically results in muscle tearing or having to be cut or (undesirably) "popping" under the round working channel right into the "field of vision."

Optionally, the working channel 18, 28, 38 includes a handle or clamping attachment or other fixing mechanism 27 (shown in phantom in FIGS. 2-4) for securing the working channel 18, 28, 38 at a particular elevation and/or angle relative to the patient. Such handle 27 may work with an extensible, bendable clamping bracket or with a rigid frame or vise (not shown) as is known in the art.

From the foregoing, it can be seen that the present invention is directed to a working channel for minimally invasive spine surgery and methods for using the same. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A working channel for separating paraspinal muscles and minimizing muscle trauma during spinal surgery comprising:
a fixed in shape elongate body having a free distal end for inserting into a patient, the elongate body having a length along a longitudinal axis of the working channel, a free proximal end for receiving surgical equipment and an interior lumen traversing through the elongate body, the distal and proximal ends of the elongate body generally corresponding to a distal and proximal end of the working channel respectively, at least a portion of the elongate body having marquise-shaped inner and outer cross-sections, the marquise-shaped inner and outer cross-sections being taken generally perpendicular to the longitudinal axis and having a width and length that are each less than the length of the elongate body, the marquise-shaped inner and outer cross-sections include first and second opposing and generally pointed corners for separating muscle fibers and first and second convex portions extending between the first and second corners, the inner and outer cross-sections being dimensionally matched at each point along the longitudinal axis.

2. The working channel of claim 1, wherein the length of the marquise-shaped outer cross-section is measured between the first and second corners and the width is measured between the first and second convex portions, the length being greater than the width.

3. The working channel of claim 1, wherein the proximal end of the elongate body includes a flared upper section and the remainder of the elongate body having a generally marquise-shaped cross section.

4. The working channel of claim 3, wherein the flared upper section is generally fixedly attached to the elongate body and is generally fixed in shape.

5. The working channel of claim 1, wherein the elongate body has constant marquise-shaped inner and outer cross sections extending between the distal and proximal ends.

6. The working channel of claim 1, wherein the working channel is configured to be inserted through an incision less than about 60 mm in span.

7. The working channel of claim 1, wherein the working channel is configured to be inserted through an incision less than about 25 mm in span.

8. The working channel of claim 1, wherein a cross-section of the proximal end of the elongate body is larger than a cross-section of the distal end of the elongate body.

9. The working channel of claim 1, wherein the elongate body includes a slot at the distal end.

10. The working channel of claim 1, further comprising only a single aperture that extends therethrough.

11. A working channel for separating paraspinal muscles and minimizing muscle trauma during spinal surgery comprising:
a flared upper section having a distal end, a proximal end and an interior lumen traversing through the flared upper section, the proximal end of the flared upper section being larger in cross section than the distal end of the flared upper section; and
a lower elongate body section extending fixedly from the distal end of the flared upper section, the lower elongate body section being rigid and having a distal end for inserting into a patient, a proximal end connected to the flared upper section and an interior lumen traversing through the lower section,
wherein the lower section has marquise-shaped inner and outer cross-sections, the marquise-shaped inner and outer cross-sections of the lower section include first and second opposing and generally pointed corners for separating muscle fibers and first and second convex portions extending between the first and second corners, the inner cross-section of the lower section being dimensionally matched to the outer cross-section thereof at each point along a longitudinal axis of the working channel.

12. The working channel of claim 11, wherein the inner and outer cross-sections of the lower elongate body section are generally uniform in length and width between the distal end and the proximal end of the lower section.

13. The working channel of claim 11, wherein a cross-section of the proximal end of the lower elongate body section is larger than a cross-section of the distal end of the lower elongate body section.

14. The working channel of claim 11, wherein the flared upper section has a marquise-shaped inner and outer cross-sections, the marquise-shaped inner and outer cross-sections of the flared upper section include first and second opposing and generally pointed corners for separating muscle fibers and first and second convex portions extending between the first and second corners.

15. The working channel of claim 11, wherein the lower elongate body section of the working channel includes a slot at the distal end.

16. The working channel of claim 11, further comprising only a single aperture that extends therethrough.

17. A method of using a working channel for separating paraspinal muscles and minimizing muscle trauma during outpatient spine surgery comprising:
a) making an incision between about 10 mm and about 100 mm in span proximate a first vertebra and a second vertebra of a spine of a patient, the incision being off-center with respect to the posterior-side of the spine of the patient and proximate to one of the laminae and the foramen of the first and second vertebrae;
b) inserting a distal end of the working channel into the incision to a desired depth proximate the first vertebra and the second vertebra of the spine accessible through the incision, the working channel having marquise-shaped inner and outer cross sections and being fixed in shape, the marquise-shaped inner and outer cross-sections being taken generally perpendicular to a longitudinal axis of the working channel, the marquise-shaped inner and outer cross-sections include first and second opposing and generally pointed corners for separating muscle fibers and first and second convex portions extending between the first and second corners; and c) accessing one of the first vertebra, the second vertebra and a small gap between the first vertebra and the second vertebra of the spine through the working channel.

18. The method according to claim 17, wherein step a) further comprises:

a-1) inserting a surgical pin proximate a first vertebra and a second vertebra of a spine of the patient prior to making the incision;

a-2) after making the incision, inserting a distal end of an insertion guide over the surgical pin proximate the small gap between the first vertebra and the second vertebra of the spine accessible through the incision, the insertion guide generally shaped and sized to fit within the interior lumen;

a-3) removing the surgical pin;

a-4) inserting a distal end of the working channel over the insertion guide proximate the small gap between the first vertebra and the second vertebra of the spine accessible through the incision; and a-5) removing the insertion guide from the working channel.

19. The method according to claim 18, wherein step a-2) further comprises:

prior to inserting the working channel, successively inserting a plurality of increasingly larger dilators the final dilator generally shaped and sized to fit within the interior lumen.

20. The method according to claim 18, further comprising:

a-1) inserting a surgical pin proximate a first vertebra and a second vertebra of a spine of the patient prior to making the incision;

a-2) after making the incision, inserting a distal end of a fascia knife over the surgical pin proximate the small gap between the first vertebra and the second vertebra of the spine accessible through the incision, the fascia knife having an elongate body and an interior lumen within the elongate body configured to receive the surgical pin; and a-3) removing the fascia knife.

21. The method according to claim 17, wherein step b) further comprises:

b-1) inserting an insertion tool into the working channel prior to inserting the working channel and then inserting the insertion tool and working channel combination into the incision; and b-2) removing the insertion tool from the working channel while leaving the working channel in the incision.

22. The method according to claim 17, wherein the proximal end of the working channel has a flared upper section.

23. The method according to claim 17 further comprising:

d) sliding the working channel along the spine, separating the paraspinal muscles for access to additional vertebrae.

24. The method according to claim 17 further comprising:

d) sliding the working channel along the spine, separating the paraspinal muscles for access to additional vertebrae.

25. A method of using a working channel for separating paraspinal muscles and minimizing muscle trauma during outpatient spine surgery comprising:

a) making an incision between about 10 mm and about 100 mm in span proximate a first vertebra and a second vertebra of a spine of a patient, the incision being off-center with respect to the posterior-side of the spine of the patient and proximate to one of the laminae and the foramen of the first and second vertebrae;

b) inserting a distal end of the working channel into the incision to a desired depth proximate the first vertebra and the second vertebra of the spine accessible through the incision, a proximal end of the working channel having a flared upper section for displacing fat and providing a larger opening to the working channel, the flared upper section having a distal end, a proximal end and an interior lumen traversing therethrough, the flared upper section having inner and outer cross-sections, the inner cross-section of the flared upper section being dimensionally matched to the outer cross-section thereof at each point along a longitudinal axis of the working channel, the proximal end of the flared upper section being larger in cross section than the distal end of the flared upper section, and a lower elongate body section extending fixedly from the distal end of the flared upper section, the lower elongate body section having a distal end for inserting into a patient, a proximal end connected to the flared upper section and an interior lumen traversing through the lower section; and c) accessing one of the first vertebra, the second vertebra and a small gap between the first vertebra and the second vertebra of the spine through the working channel.

26. The method according to claim 25 further comprising:

d) sliding the working channel along the spine, separating the paraspinal muscles for access to additional vertebrae.

* * * * *